United States Patent [19]

Mizukawa et al.

[11] Patent Number: 5,122,612
[45] Date of Patent: Jun. 16, 1992

[54] PROCESS FOR PRODUCING 5-AMINO-4-HALOGENO-1H-PYRAZOLE COMPOUNDS

[75] Inventors: Yuki Mizukawa; Keizo Kimura; Tadahisa Sato, all of Minami-ashigara, Japan

[73] Assignee: Fuji Photo Film Co., Ltd., Kanagawa, Japan

[21] Appl. No.: 723,050

[22] Filed: Jun. 28, 1991

[30] Foreign Application Priority Data

Jul. 2, 1990 [JP] Japan .................................. 1-172635

[51] Int. Cl.$^5$ ........................................... C07D 231/38
[52] U.S. Cl. ................................................. 548/362
[58] Field of Search ........................................ 548/362

[56] References Cited

U.S. PATENT DOCUMENTS 4,812,576  3/1989  Wolff et al. ........................ 548/362

OTHER PUBLICATIONS

Chemical Abstracts, Fuji Photo Film Co. et al, "5-Amino-4-chloro-3-methyl-1H-pyrazole hydrochloride", May 15, 1989, vol. 110, No. 20, p. 102, column 2.

Chemical Abstracts, Konishiroku Photo Industry Co. et al, "Preparation of 5-amino-1H-pyraxoles as intermediates for 1H-pyrazolo (3,2-c)-s-triazole couplers for photography", Dec. 19, 1988, vol. 109, No. 25, p. 861, column 2.

Chemical Abstracts, Konishiroku Photo Industry Co., LDT et al, "Preparation of 5-amino-1H-pyrazoles as intermediates for magenta couplers", Feb. 29, 1988, vol. 108, No. 9, p. 682, col. 2.

*Primary Examiner*—Robert W. Ramsuer
*Attorney, Agent, or Firm*—Burns, Doane, Swecker & Mathis

[57] ABSTRACT

There is disclosed a process for producing 5-amino-4-halogeno-1H-pyrazole compounds comprising reacting a compound represented by the following formula (I) with a halogenating agent to obtain a compound represented by the following formula (II):

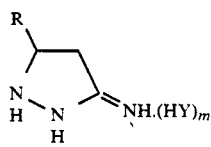

Formula (I):

wherein R represents a hydrogen atom, an alkyl group, or an aryl group, m is 0 or an integer, and Y represents an organic or inorganic acid radical,

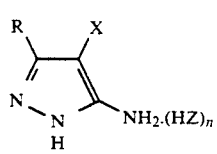

Formula (II):

wherein R has the same meaning as defined above in formula (I), X represents a halogen atom, n is 0 or an integer, and Z represents an organic or inorganic acid radical.

20 Claims, No Drawings

PROCESS FOR PRODUCING 5-AMINO-4-HALOGENO-1H-PYRAZOLE COMPOUNDS

FIELD OF THE INVENTION

The present invention relates to a process for producing, at a low cost easily on an industrial scale, 5-amino-4-halogeno-1H-pyrazole compounds that are useful intermediates for synthesizing 1H-pyrazoloazole couplers, such as a 1H-pyrazolo-[1,5-b]-1,2,4-triazole coupler and a 1H-pyrazolo[3,2-c]-1,2,4-triazole coupler, which are used as intermediate materials for dyes for silver halide color photographic materials and dyes for photographs, the thermal transfer process, color electrophotographs, and printing.

BACKGROUND OF THE INVENTION

It is known that 1H-pyrazoloazole couplers, such as 1H-pyrazolo[1,5-b]-1,2,4-triazole compounds and 1H-pyrazolo[3,2-c]-1,2,4-triazole compounds, are magenta couplers that give excellent hue, as respectively described in U.S. Pat. Nos. 4,540,654 and 3,725,067. 1H-pyrazolo[1,5-c]-tetrazole couplers, 1H-imidazo[1,2-b]pyrazole couplers, and 1H-pyrazolo[1,5-a]benzimidazole couplers are also described in JP-A ("JP-A" means unexamined published Japanese patent application) Nos. 33552/1985 and 162548/1984 and U.S. Pat. No. 3,061,432, respectively. 1H-pyrazoloazole compounds are known as cyan couplers in JP-A No. 264753/1988.

Processes for synthesizing these pyrazoloazole compounds are described, for example, in JP-A Nos. 190779/1985, 197688/1985, 215687/1985, 145163/1986, 18780/1986, and 249969/1986.

In these processes for synthesizing pyrazoloazole compounds, various compounds are reported as synthetic intermediates, and among these, 5-amino-4-halogeno-1H-pyrazole compounds are important.

For example, JP-A Nos. 239272/1988 and 6274/1989 describe 5-amino-4-halogeno-1H-pyrazoles as starting material that will lead to 1H-pyrazolo[1,5-b]-1,2,4-triazoles, and JP-A Nos. 249969/1986, 10068/1987, and 252773/1987 describe 5-amino-4-halogeno-1H-pyrazoles as starting material that will lead to 1H-pyrazolo[3,2-c]-1,2,4-triazoles. Thus, 5-amino-4-halogeno-1H-pyrazoles are quite useful synthetic intermediates in the synthesis of pyrazolotriazole compounds, and all the processes for the synthesis thereof involve halogenation of 5-amino-1H-pyrazoles. Major examples are:

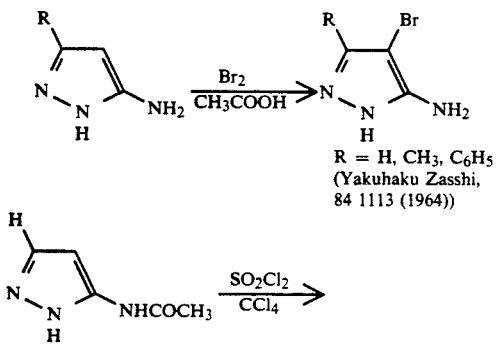

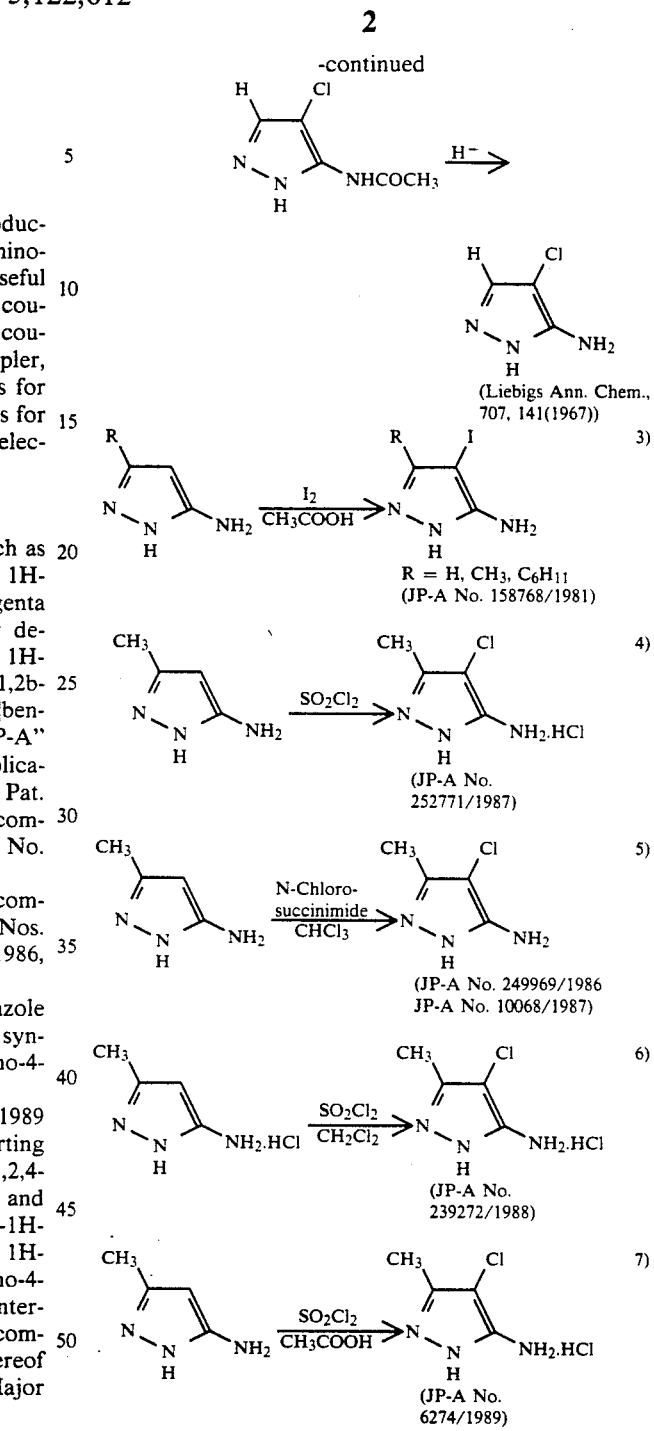

Although processes for the synthesis of 5-amino-1H-pyrazoles as starting materials are described, for example, in the Journal of American Chemical Society, page 144 (1945), U.S. Pat. No. 2,987,523, JP-B ("JP-B" means examined Japanese patent publication) No. 26082/1970, the Journal of Heterocyclic Chemistry, Vol. 11, page 423 (1974), and JP-A Nos. 65245/1986 and 236768/1986, they are accompanied by such problems as that many steps are involved and starting materials are expensive and not readily available. Therefore, as long as these starting materials are used, similar problems are involved in the synthesis of 5-amino-4-halogeno-1H-pyrazoles, which are desired to be solved.

SUMMARY OF THE INVENTION

The object of the present invention is to provide a process for synthesizing a 5-amino-4-halogeno-1H-pyrazole compound that is industrially useful and advantageous from the standpoint of the number of steps and the process cost.

Other and further objects, features, and advantages of the invention will appear more fully from the following description.

DETAILED DESCRIPTION OF THE INVENTION

In order to solve the above problems, the inventors have keenly studied to develop particularly a process wherein 5-amino-1H-pyrazole compounds are not used as starting material, and they have found that 5-amino-4-halogeno-1H-pyrazoles can directly be synthesized by halogenating 3-iminopyrazolidines, and that when $\alpha,\beta$-unsaturated nitriles are used as synthesis raw materials for the raw material in the preceding step, the raw materials are obtained relatively inexpensively and 5-amino-4-halogeno-1H-pyrazole compounds can be synthesized with a small number of steps, which finding has led to the present invention.

That is, the present invention provides (1) a process for producing 5-amino-4-halogeno-1H-pyrazole compounds, which comprises reacting a compound represented by the following formula (I) with a halogenating agent to obtain a compound represented by the following formula (II):

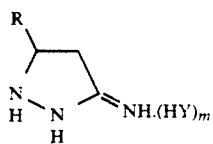

Formula (I):

wherein R represents a hydrogen atom, an alkyl group, or an aryl group, m is 0 or an integer, and Y represents an organic or inorganic acid radical,

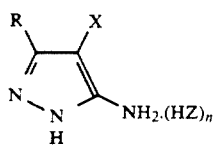

Formula (II):

wherein R has the same meaning as defined above in formula (I), X represents a halogen atom, n is 0 or an integer, and Z represents an organic or inorganic acid radical, and (2) a process as stated in (1), wherein the compound represented by formula (I) is obtained by reacting an $\alpha,\beta$-unsaturated nitrile compound represented by the following formula (III) with hydrazine:

Formula (III)

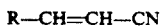

R—CH=CH—CN wherein R has the same meaning as defined above in formula (I).

The present invention will now be described in detail.

In the present invention, the synthesis of a 5-amino-4-halogeno-1H-pyrazole of formula (II) from a 3-iminopyrazolidine of formula (I) is represented by the following formula:

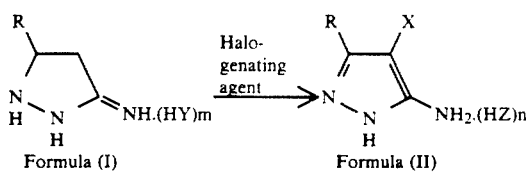

Although the reaction conditions vary depending on the raw materials used, as a solvent, a hydrocarbon solvent, such as hexane, an aromatic solvent, such as benzene and toluene, an ether solvent, such as tetrahydrofuran and dioxane, an alcohol solvent, such as methanol and ethanol, an amide solvent, such as N,N-dimethylformamide, an ester solvent, such as ethyl acetate, a halogen solvent, such as methylene chloride and ethylene chloride, or sulfolane, dimethylsulfoxide, or acetonitrile is used. These solvents may be used alone or in combination. Preferably an amide solvent, an ester solvent, or sulfolane is used. As the halogenating agent, a chlorinating agent, such as sulfuryl chloride and chlorine, a brominating agent, such as bromine, or an iodinating, such as iodine, is used. The halogenating agent is preferably used in such a molar ratio that 2 to 5 equivalents, more preferably 2 to 3 equivalents, based on the compound represented by formula (I). The reaction temperature is preferably in the range of $-20°$ to $200°$ C., more preferably $0°$ to $150°$ C. The reaction time is preferably in the range of 10 min to 10 hours, more preferably 30 min to 5 hours. However, the conditions are not restricted to those mentioned.

It seems that the reaction proceeds in steps and a reaction intermediate that cannot be isolated due to its instability is observed on TLC. The intermediate seems to be a dihalide of the 3-iminopyrazolidine, but its structure has not been identified.

In many cases, the 5-amino-4-halogeno-1H-pyrazole compound obtained by the process of the present invention is produced in the form of a salt of the organic acid or inorganic acid derived from the used halogenating agent. The thus obtained salt of an organic acid or inorganic acid of the 5-amino-4-halogeno-1H-pyrazole can be isolated in the form of a free pyrazole compound by neutralizing the salt, for example, with an aqueous potassium carbonate solution or an aqueous sodium hydroxide, and if a suitable other acid is added to the free pyrazole compound, it can be isolated in the form of a salt of the other organic or inorganic acid.

The step of synthesizing a 3-iminopyrazolidine represented by formula (I) using an $\alpha,\beta$-unsaturated nitrile of formula (III) can be represented by the following formula:

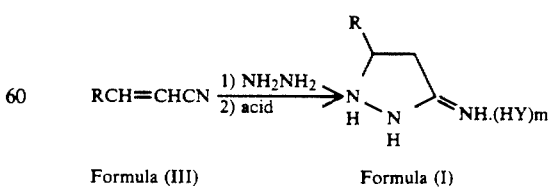

Although $\alpha,\beta$-unsaturated nitriles represented by formula (III) are relatively inexpensive and readily available (e.g., crotononitrile, 2-pentenenitrile, and cinnamonitrile), they can be synthesized from the more readily available corresponding aldehydes or saturated nitriles.

The synthesis of the 3-iminopyrazolidine of formula (I) from the α,β-unsaturated nitrile of formula (III) is carried out by reacting it first with hydrazine, to synthesize a compound A given below, followed by treatment with an acid.

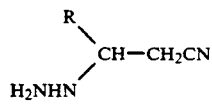

Compound A

The reaction for obtaining A is carried out without a solvent or in a solvent such as an alcohol. As the hydrazine, either hydrazine anhydride or hydrazine hydrate may be used. If hydrazine hydrate is used, the water must be removed before the synthesis of the 3-iminopyrazolidine. The reaction temperature is 0° to 60° C., preferably 5° to 40° C. The reaction time is 1 to 5 hours, preferably 2 to 3 hours. The ring closing reaction from A to the compound represented by formula (I) is generally carried out in an alcohol solvent. The acid used is an organic or inorganic acid, and the organic acid that can be used include methanesulfonic acid, p-toluenesulfonic acid, benzenesulfonic acid, trifluoromethanesulfonic acid, and trifluoroacetic acid; the inorganic acids that can be used include, hydrochloric acid, hydrobromic acid, and sulfuric acid. Preferably an inorganic acid is used, and more preferably a hydrohalogenic acid is used. When hydrochloric acid or a hydrobromic acid that is a hydrohalogenic acid is used, it is preferably used in the form of a gas. The reaction temperature is such that when the acid is added the temperature is 0° to 50° C., preferably 10° to 30°, initially, and thereafter the reaction mixture is heated in the alcohol used under reflux. The reaction time is 30 min to 5 hours, preferably 2 to 3 hours. The 3-iminopyrazolidine of formula (I) generally deposits as crystals from the reaction liquid and can be separated and purified by filtration under suction.

When R=H, for the synthesis of the 3-iminopyrazolidine, reference will be made to Organic Synthesis, Vol. V, page 39 (1973).

Reaction components used in the present process will now be described.

In formulae (I), (II), and (III), R represents a hydrogen atom, an alkyl group, or an aryl group.

The alkyl group represented by R includes a linear or branched alkyl group, aralkyl group, alkenyl group, alkynyl group, cycloalkyl group, and cycloalkenyl group having 1 to 32, preferably 1 to 20, carbon atoms, which may be substituted by a halogen atom, a nitro group, an amino group, or a substituent that bonds through an oxygen atom, a nitrogen atom, a sulfur atom, or a carbonyl group, such as methyl, ethyl, isopropyl, n-propyl, n-butyl, t-butyl, tridecyl, heptadecyl, 2-methanesulfonylethyl, 3-(3-pentadecylphenoxy)propyl, phenylethyl, 2-methyl-2-nitropropyl, 2-ethoxytridecyl, trifluoromethyl, cyclopentyl, cyclohexyl, and 3-(2,4-di-t-amylphenoxy)propyl. The aryl group represented by R includes an aryl group having 6 to 32, preferably 6 to 20, carbon atoms, which may be substituted by a substituent that bonds through an oxygen atom, a nitrogen atom, a sulfur atom, or a carbonyl group, an alkyl group, an amino group, a nitro group, or a halogen atom. As a substituent, it can be mentioned an alkoxy group having 1 to 4 carbon atoms, an alkyl group having 1 to 4 carbon atoms, a halogen atom (e.g., Cl and Br), a nitro group, a carbamoyl group, a alkanesulfonyl group having 1 to 24 carbon atoms, an alkoxysulfonyl group having 1 to 4 carbon atoms, and an alkyl-substituted amino group. The aryl group represented by R is preferably a phenyl group which may be substituted by the above-mentioned group, and it can be mentioned, for example, such as phenyl, 2-chlorophenyl, 4-t-butylphenyl, 2,4-di-t-amylphenyl, 3,5-nitrophenyl, 4-methoxyphenyl, 3-nitro-4-chlorophenyl, 3,5-carbamolylphenyl, 4-nitro-2-methoxysulfonylphenyl, 2-chloro-4-nitrophenyl, 3,5-dinitro-4-chlorophenyl, 4-nitrophenyl, 2-nitro-3,5-dodecylsulfonylphenyl, 2,4-methoxyphenyl, 2-methoxyphenyl, 2,5-methoxyphenyl, and 2-dimethylaminophenyl.

In formula (II), X represents a halogen atom, preferably a chlorine atom, a bromine atom, or an iodine atom. In formulae (I) and (II), Y and Z each represent an organic or inorganic acid radical, and typical examples thereof include organic acid radicals, such as $CH_3SO_3^\ominus$, $C_6H_5SO_3^\ominus$, $CH_3C_6H_4SO_3^\ominus$, $CF_3SO_3^\ominus$, $CCl_3SO_3^\ominus$, $CF_3COO^\ominus$, $CH_3COO^\ominus$, $CCl_3COO^\ominus$, $C_6H_5COO^\ominus$, and

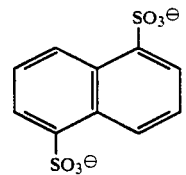

and inorganic acid radicals, such as $Cl^\ominus$, $Br^\ominus$, $I^\ominus$, $HSO_4^\ominus$, $NO_3^\ominus$, and $ClO_4^\ominus$. An inorganic acid radical is preferable, and $Cl^\ominus$, $Br^\ominus$, or $I^\ominus$ are more preferable.

In formula (I) and (II), m and n each are 0 or an integer, preferably 0 to 3, more preferably 0 to 2.

Specific examples of the compound represented by formula (III) are shown below, but the present invention is not restricted to them.

| | |
|---|---|
| $CH_3CH=CHCN$ | (III-1) |
| $(t)C_4H_9CH=CHCN$ | (III-2) |
| $CH_2=CHCN$ | (III-3) |

  (III-4)

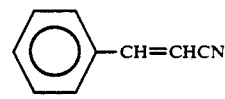  (III-5)

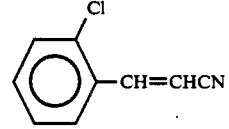  (III-6)

(n)$C_4H_9CH=CHCN$  (III-7)

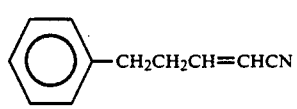  (III-8)

(i)$C_3H_7CH=CHCN$  (III-9)

-continued
(n)C₁₇H₃₅CH=CHCN
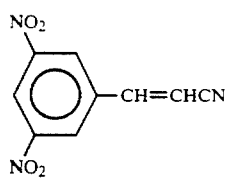 (III-10)
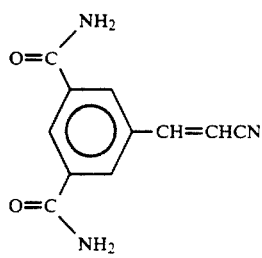 (III-11)
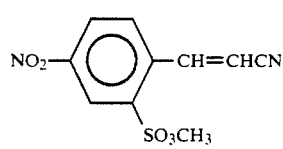 (III-12)
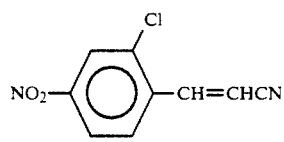 (III-13)
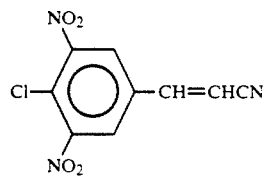 (III-14)
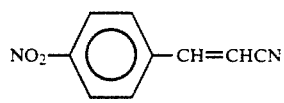 (III-15)
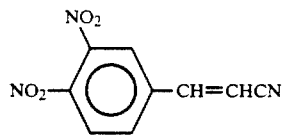 (III-16)
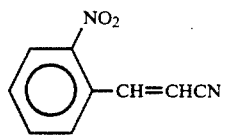 (III-17)
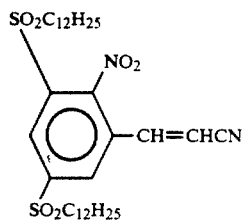 (III-18)
-continued
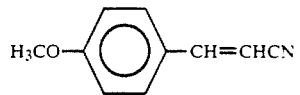 (III-19)
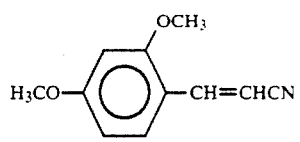 (III-20)
Now, typical examples of the 5-amino-4-halogeno-1H-pyrazole compound that can be produced by the present process are shown below, but the present invention is not restricted to them.
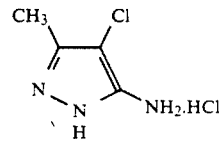 II-1)
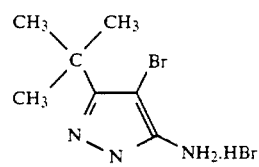 II-2)
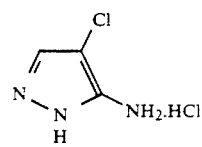 II-3)
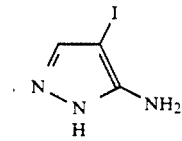 II-4)
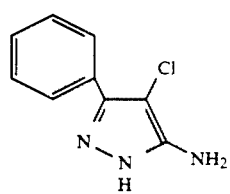 II-5)
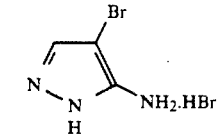 II-6)
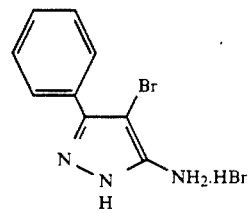 II-7)

-continued
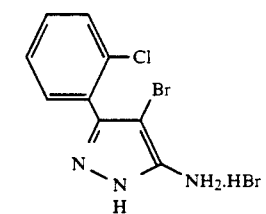 II-8)
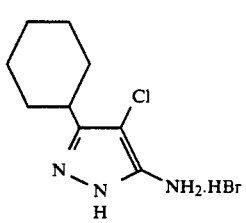 II-9)
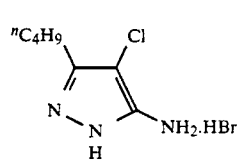 II-10)
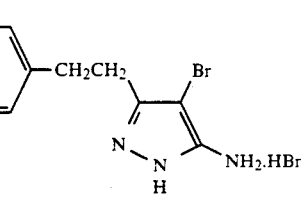 II-11)
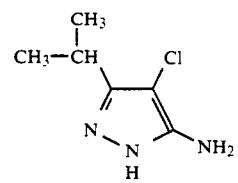 II-12)
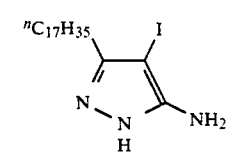 II-13)
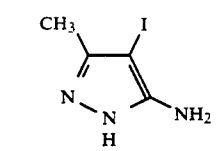 II-14)
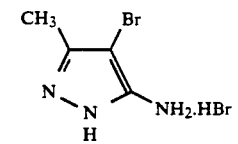 II-15)
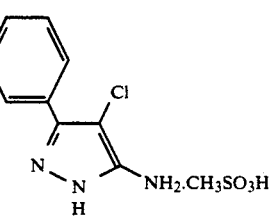 II-16)
-continued
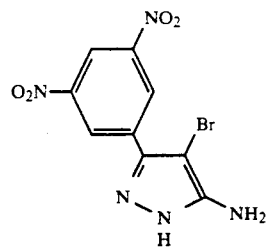 II-17)
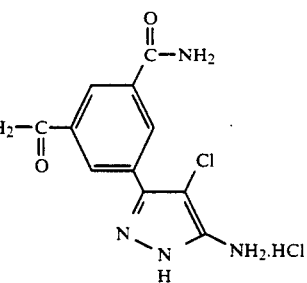 II-18)
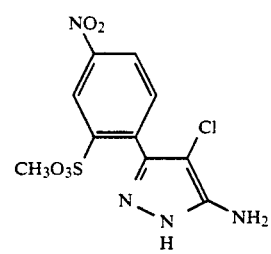 II-19)
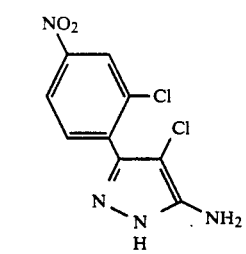 II-20)
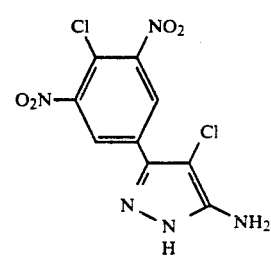 II-21)
II-22)

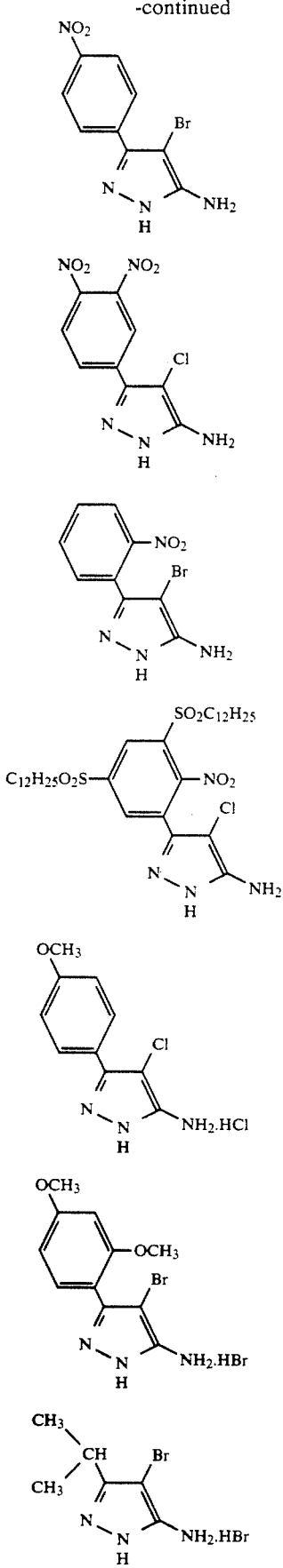

According to the present invention, a 5-amino-4-halogeno-1H-pyrazole compound that is an important synthetic intermediate for a 1H-pyrazoloazole compound useful as a color photographic coupler, such as 1H-pyraz-olo[1,5-b]-1-,2,4-triazole and 1H-pyrazolo[3,2-c]-1,2,4-triazole, can be synthesized effectively in a good yield. Further, according to the present invention, various 5-amino-1H-pyrazoles can be synthesized by using relatively inexpensive and readily available starting materials, the process of the present invention serves as a process for producing synthetic intermediates for pyrazoloazoles as photographic couplers, and therefore the industrial value of the present invention is high. As a result, the practical value of these pyrazoloazoles as photographic couplers can be increased further.

Now the present invention will be described in more detail with reference to the following Examples, wherein the Nos. of compounds correspond to those of exemplified compounds.

EXAMPLE 1

Synthesis of Exemplified Compound (II-I)

738 g of crotononitrile was added dropwise to 625 g of hydrazine hydrate (an aqueous solution having a content of 80%) with stirring, while the internal temperature was kept at 40° C. or below under water cooling. Thereafter stirring was continued for 3 hours and then the reaction mixture was allowed to stand overnight. 1.8 liter of toluene was added to the reaction mixture, the mixture was heated with stirring under reduced pressure by an aspirator while the toluene was refluxed with the internal temperature kept within the range of 75° to 80° C., and the water separated was removed using a Barrett distilling receiver. When the separation of water stopped, the mixture was cooled with ice, 1.3 liter of methanol was added, and then 402 g of hydrochloric acid gas was blown into the mixture while the internal temperature was kept at 20° to 25° C. Thereafter heating was continued for 3 hours under reflux, and then the reaction mixture was cooled with ice and stirred for 30 min with the internal temperature kept at 10° C. or below. The thus obtained crystals were filtered under suction, to yield the desired 3-imino-5methylpyrazolidine hydrochloride in an amount of 1150 g (85% yield).

540 ml of N,N-dimethylformamide was added to 542 g of the obtained 3-imino-5-methylpyrazolidine hydrochloride, and they were stirred under water cooling. Then 709 ml of sulfuryl chloride was added dropwise thereto while the internal temperature was kept at 30° C. or below. After the reaction mixture was stirred for a further 1 hour with the internal temperature kept at 30° C. or below, 540 ml of ethyl acetate was added and the reaction mixture was heated and stirred under reflux for 1 hour. Thereafter the mixture was cooled with water to bring the internal temperature to 20° C., and it was stirred for 1 hour; then the resulting crystals were filtered under suction, to yield the desired exemplified compound (II-I) in an amount of 591 g (88% yield).

Melting point: 210° C. (decomp.)
NMR (DMSO-d$_6$):δ=8.0 (brs, 4H), 2.22 (s, 3H)

EXAMPLE 2

274 g of hydrazine hydrochloride was added to 804 ml of a 28% solution of sodium methoxide in methanol, and after they were stirred for 4 hours at room temperature, 295 g of crotononitrile was added dropwise thereto under water cooling while the internal temperature was kept at 40° C. Thereafter stirring was continued for 3 hours; then the mixture was cooled with ice, and 161 g of hydrochloric acid was blown into it with the internal temperature kept at 25° C. or below. Then, after 1 liter of ethyl acetate was added thereto, the mixture was heated to distill off 1.5 liter of the solvent, and then 700 ml of ethyl acetate was added. The mixture was heated under reflux for 3 hours with stirring; then it was cooled with water, and stirred for 30 min with the internal temperature kept at 15° C. or below, and then the resulting crystals were filtered under suction, to yield 709 g of a mixture of the desired 3-imino-5-methylpyrazolidine and sodium chloride. The purity of the mixture was determined by NMR to be 57.9 wt. % (internal standard : ethylene glycol). The true yield was 411 g (76% yield).

EXAMPLE 3

Synthesis of Exemplified Compound (II-2)

222 ml of sulfolane was added to 222 g of 5-tert-butyl-3-imino-3-pyrazolidine hydrobromide synthesized from 3-tert-butylacrylonitrile in accordance with the method shown in Example 1, and they were stirred under ice cooling. 336 g of bromide was added dropwise thereto while the internal temperature was kept at 20° C. or below. Then, after the reaction mixture was stirred for 1 hour with the internal temperature kept at 30° C. or below, 300 ml of isopropyl alcohol was added and the mixture was heated under reflux for one hour with stirring. Thereafter the isopropyl alcohol was distilled off under the action of an aspirator with the external temperature kept at 70° C., then 300 ml of acetonitrile was added to the residue, the mixture was stirred for one hour with the internal temperature kept at 10° C. or below under ice cooling, and the resulting crystals were filtered under suction, to yield crystals of the desired exemplified compound (II-2) in an amount of 245 g (82 % yield).

Melting point: 144.0° to 146.5° C.
NMR (DMSO-d$_6$)δ=10.1 (brs. 4H), 1.38 (s, 9H)

EXAMPLE 4

Synthesis of Exemplified Compound (II-5)

200 ml of N,N-dimethylformamide was added to 198 g of 3-imino-5-phenyl-3-pyrazolidine hydrochloride synthesized from cinnamonitrile in accordance with the method shown in Example 1, and they were stirred under water cooling. Then 242 ml of sulfuryl chloride was added dropwise thereto while the internal temperature was kept at 20° C. or below. After the mixture was stirred for a further 2 hours while the internal temperature was kept at 30° C. or below, 200 ml of benzene was added and the reaction mixture was heated under reflux for 2 hours with stirring. Thereafter the internal temperature was brought to 10° C. or below under ice cooling, the mixture was stirred for 1 hour, and the resulting crystals were filtered under suction and dried. Then 2 liter of water was added to the crystals, and after a solution of 36 g of sodium hydroxide in 100 ml of water was added to the mixture with vigorous stirring, 20 g of sodium hydrogen carbonate was added thereto, followed by stirring for 1 hour, and the crystals were filtered under suction. In this manner, the desired exemplified compound (II-5) was obtained in an amount of 141 g (73% yield).

Melting point: 108.0° to 109.5° C.
NMR (DMSO-d$_6$)δ=9.92 (s, 1H), 7.3-7.9 (m, 5H), 7.5 (brs, 2H)

EXAMPLE 5

Synthesis of Exemplified Compound (II-32)

88 ml of N,N-dimethylformamide was added to 88.3 g of 5-tert-butyl-3-imino-3-pyrazolidine hydrochloride synthesized from 3-tert-butylacrylonitrile in accordance with the method shown in Example 1, and they were stirred under ice cooling. 88.7 ml of sulfuryl chloride was added dropwise thereto while the internal temperature was kept at 15° C. or below. Then, after the reaction mixture was stirred for 1 hour with the internal temperature kept at 30° C. or below, 88 ml of ethyl acetate was added and the mixture was heated under reflux for one hour with stirring. Thereafter the mixture was stirred for one hour with the internal temperature kept at 20° C. or below under water cooling, and the resulting crystals were filtered under suction, to yield crystals of the desired exemplified compound (II-32) in an amount of 76.7 g (73% yield).

Melting point: 154.0° to 155.5° C.

NMR (DMSO-d$_6$)δ=10.4 (brs. 4H), 1.37 (s, 9H)

Having described our invention as related to the present embodiments, it is our intention that the invention not be limited by any of the details of the description, unless otherwise specified, but rather be construed broadly within its spirit and scope as set out in the accompanying claims.

What we claim is:

1. A process for producing 5-amino-4-halogeno-1H-pyrazole compounds, which comprises reacting a compound represented by the following formula (I) with a halogenating agent to obtain a compound represented by the following formula (II):

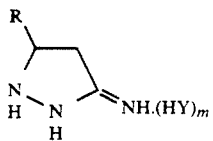

Formula (I):

wherein R represents a hydrogen atom, an alkyl group, an aralkyl group, an alkenyl group, an alkynyl group, a cycloalkyl group, a cycloalkenyl group, or an aryl group, m is 0 or an integer, and Y represents an organic or inorganic acid radical, Formula (II):

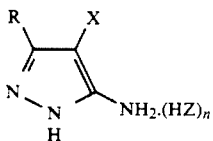

Formula (II):

wherein R has the same meaning as defined above in formula (I), X represents a halogen atom, n is 0 or an integer, and Z represents an organic or inorganic acid radical.

2. The process as claimed in claim 1, wherein the compound represented by formula (I) is obtained by reacting an α,β-unsaturated nitrile compound represented by the following formula (III) with hydrazine:

Formula (III)

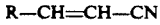

R—CH=CH—CN wherein R represents a hydrogen atom, an alkyl group or an aryl group.

3. The process as claimed in claim 1, wherein one or more solvents selected from the group consisting of hydrocarbons, aromatic solvents, ether solvents, alcohol solvents, amide solvents, ester solvents, halogen solvents, sulfolane, dimethylsulfoxide and acetonitrile is used as a solvent in the halogenating reaction.

4. The process as claimed in claim 1, wherein an amide solvent, an ester solvents or sulfolane is used as a solvent in the halogenating reaction.

5. The process as claimed in claim 1, wherein the halogenating agent is selected form the group consisting of chlorinating agents, brominating agents and iodinating agents.

6. The process as claimed in claim 1, wherein the halogenating agent is used in such a molar amount that 2 to 5 equivalents of the halogenating agent are present based on the compound represented by formula (I).

7. The process as claimed in claim 1, wherein the temperature of halogenating reaction is in the range of −20° to 200° C.

8. The process as claimed in claim 1, wherein the reaction time of halogenating reaction is in the range of 10 min to 10 hours.

9. The process as claimed in claim 2, wherein the compound represented by formula (I) is obtained by reacting α,β-unsaturated nitrile of formula (III) with hydrazine to synthesize compound A represented by the formula shown below followed by treatment with an acid:

Compound A wherein R represents a hydrogen atom, an alkyl group or an aryl group.

10. The process as claimed in claim 9, wherein the synthesis reaction of compound A is carried out at a temperature of 0° C. to 60° C. for one to five hours.

11. The process as claimed in claim 9, wherein for the treatment of compound A the acid is selected from methanesulfonic acid, p-toluenesulfonic acid, benzenesulfonic acid trifluoromethanesulfonic acid, trifluoroacetic acid, hydrochloric acid, hydrobromic acid and sulfuric acid.

12. The process as claimed in claim 9, wherein the acid for treatment of compound A is hydrochloric acid or hydrobromic acid in the form of a gas.

13. The process as claimed in claim 1, wherein the group represented by R in formulae (I) and (II) is selected from the group consisting of alkyl group, aralkyl group, alkenyl group, alkynyl group, cycloalkyl group, and cycloalkenyl group.

14. The process as claimed in claim 1, wherein the aryl group represented by R in formula (I) and (II) is an aryl group which may be substituted by a substituent that bonds through an oxygen atom, a nitrogen atom, a sulfur atom, or a carbonyl group, an alkyl group, an amino group, a nitro group, or a halogen atom.

15. The process as claimed in claim 1, wherein the aryl group represented by R in formulae (I) and (II) is selected from the group consisting of phenyl group, 2-chlorophenyl group, 4-t-butylphenyl group, 2,4-di-t-aminophenyl group, 3,5-nitrophenyl group, 4-methoxyphenyl group, 3-nitro-4-chlorophenyl group, 3,5-carbamolylphenyl group, 4-nitro-2-methoxysulfonylphenyl group, 2-chloro-4-nitrophenyl group, 3,5-dinitro-4-chlorophenyl group, 4-nitrophenyl group, 2-nitro-3,5-dodecylsulfonylphenyl group, 2,4-methoxyphenyl group, 2-methoxyphenyl group, 2,5-methoxyphenyl group, and 2-dimethylaminophenyl group.

16. The process as claimed in claim 1, wherein the halogen atom represented by X in formula (II) is selected from the group consisting of a chlorine atom, a bromine atom, and iodine atom.

17. The process as claimed in claim 1, wherein the acid radical represented by Y in formula (I) is selected from the group consisting of CH$_3$SO$_3$⊖, C$_6$H$_5$SO$_3$⊖, $CH_3C_6H_4SO_3^\ominus$, $CF_3SO_3^\ominus$, $CCl_3SO_3^\ominus$, $CF_3COO^\ominus$, $CH_3COO^\ominus$, $CCl_3COO^\ominus$, $C_6H_5COO^\ominus$, and

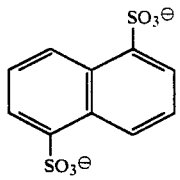

$Cl^\ominus$, $Br^\ominus$, $I^\ominus$, $HSO_4^\ominus$, $NO_3^\ominus$, and $ClO_4^\ominus$.

18. The process as claimed in claim 1, wherein the acid radical represented by Y in formula (I) is $Cl^\ominus$, $Br^\ominus$, or $I^\ominus$.

19. The process as claimed in claim 1, wherein the acid radical represented by Z in formula (I) is selected from the group consisting of $CH_3SO_3^\ominus$, $C_6H_5SO_3^\ominus$, $CH_3C_6H_4SO_3^\ominus$, $CF_3SO_3^\ominus$, $CCl_3SO_3^\ominus$, $CF_3COO^\ominus$, $CH_3COO^\ominus$, $CCl_3COO^\ominus$, $C_6H_5COO^\ominus$, and

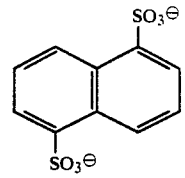

$Cl^\ominus$, $Br^\ominus$, $I^\ominus$, $HSO_4^\ominus$, $NO_3^\ominus$, and $ClO_4^\ominus$.

20. The process as claimed in claim 1, wherein the acid radical represented by Z in formula (I) is $Cl^\ominus$, $Br^\ominus$, or $I^\ominus$.

* * * * *